(12) United States Patent
Schermeier et al.

(10) Patent No.: US 11,133,097 B2
(45) Date of Patent: Sep. 28, 2021

(54) MEDICAL TREATMENT SYSTEM

(71) Applicant: FRESENIUS MEDICAL CARE DEUTSCHLAND GMBH, Bad Homburg (DE)

(72) Inventors: Olaf Schermeier, Frankfurt am Main (DE); Kirill Koulechov, Shanghai (CN); Peter Eifler, Frankfurt am Main (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 203 days.

(21) Appl. No.: 16/341,929

(22) PCT Filed: Oct. 27, 2017

(86) PCT No.: PCT/EP2017/077604
§ 371 (c)(1),
(2) Date: Apr. 15, 2019

(87) PCT Pub. No.: WO2018/078099
PCT Pub. Date: May 3, 2018

(65) Prior Publication Data
US 2019/0244703 A1  Aug. 8, 2019

(30) Foreign Application Priority Data

Oct. 28, 2016  (DE) ..................... 10 2016 221 337.7

(51) Int. Cl.
*A61M 1/16* (2006.01)
*G16H 20/40* (2018.01)
(Continued)

(52) U.S. Cl.
CPC .............. *G16H 20/40* (2018.01); *A61M 1/14* (2013.01); *G16H 10/65* (2018.01); *G16H 40/40* (2018.01);
(Continued)

(58) Field of Classification Search
CPC ........ G16H 40/67; G16H 20/17; G16H 10/60; G16H 40/63; G16H 40/20; G16H 40/60;
(Continued)

(56) References Cited

U.S. PATENT DOCUMENTS

2005/0065817 A1*  3/2005  Mihai .................. A61B 5/0002
705/2
2009/0037216 A1  2/2009  Bluemler et al.
(Continued)

FOREIGN PATENT DOCUMENTS

DE  102005025516 A1  12/2006
DE  102012012350 A1  12/2013
(Continued)

OTHER PUBLICATIONS

Search Report issued in corresponding German Patent Application No. 10 2016 221 337.7 dated Jun. 1, 2017 (14 pages).
(Continued)

*Primary Examiner* — Maroun P Kanaan
(74) *Attorney, Agent, or Firm* — Kilyk & Bowersox, P.L.L.C.

(57) ABSTRACT

The invention concerns a medical treatment system (1), comprising:
a medical treatment device (10), wherein the medical treatment device comprises input means (11) for selecting a treatment, wherein the medical treatment device comprises a device (12) for generating a patient-related and a treatment-related request code, wherein the request code is presented (13) on the medical treatment device (10),
a therapy-enabling device (20), wherein the therapy-enabling device (20) comprises a device (21) for receiving request code data, wherein the therapy-enabling device (20) furthermore comprises an enabling
(Continued)

code generating device (22) which, as a function of a received request code and stored data (DB), decides whether an enabling code will be generated and sends the generated request code (23), wherein the medical treatment device (10) furthermore comprises means for entering an enabling code (11, 14), wherein the medical treatment device (10) decides, at least as a function of the enabling code and optionally the previously generated request code, whether and if necessary how the requested treatment will be enabled.

20 Claims, 2 Drawing Sheets

(51) Int. Cl.
  *A61M 1/14* (2006.01)
  *G16H 40/63* (2018.01)
  *G16H 10/65* (2018.01)
  *G16H 40/40* (2018.01)

(52) U.S. Cl.
  CPC ..... *G16H 40/63* (2018.01); *A61M 2205/3561* (2013.01); *A61M 2205/52* (2013.01)

(58) Field of Classification Search
  CPC ........ G16H 20/10; G16H 15/00; G16H 20/30; G16H 30/20; G16H 30/40; G16H 40/40; G16H 10/65; G16H 20/40; G16H 10/40; G16H 50/20; G16H 20/13; G16H 50/30; G16H 80/00; G16H 50/70; G16H 70/20; G16H 70/40; H04L 67/12; H04L 63/0236; H04L 63/0428; H04W 4/70; H04W 88/02; H04W 84/18; H04W 4/50; H04W 4/80; A61B 5/0022; A61B 5/11; A61B 5/411; A61B 5/4839; A61B 2560/0271

See application file for complete search history.

(56) References Cited

U.S. PATENT DOCUMENTS

| | | |
|---|---|---|
| 2011/0209212 A1 | 8/2011 | Newlin et al. |
| 2012/0185267 A1* | 7/2012 | Kamen ............... A61B 5/0024 705/2 |
| 2013/0345623 A1 | 12/2013 | Kopperschmidt et al. |
| 2014/0194817 A1 | 7/2014 | Lee et al. |
| 2014/0288947 A1* | 9/2014 | Simpson ................ G16H 20/40 705/2 |
| 2014/0359715 A1 | 12/2014 | Apell et al. |
| 2015/0230760 A1* | 8/2015 | Schneider ............. G16H 20/17 600/300 |
| 2016/0022892 A1 | 1/2016 | Eifler et al. |
| 2018/0001010 A1* | 1/2018 | Blumler ................. H04L 63/08 |

FOREIGN PATENT DOCUMENTS

| | | |
|---|---|---|
| DE | 102013008418 A1 | 11/2014 |
| WO | 2006086735 A2 | 8/2006 |
| WO | 2007051118 A2 | 5/2007 |
| WO | 2014001970 A2 | 1/2014 |

OTHER PUBLICATIONS

International Search Report and Written Opinion issued in corresponding International Patent Application No. PCT/EP2017/077604 (with English translation) dated Mar. 1, 2018 (29 pages).

* cited by examiner

MEDICAL TREATMENT SYSTEM

This application is a National Stage Application of PCT/EP2017/077604, filed Oct. 27, 2017, which claims priority to German Patent Application No. 10 2016 221 337.7, filed Oct. 28, 2016.

Patient safety is a major problem in many areas of medical technology.

In this regard, it should be noted that, on cost grounds, recurring treatments are transferred onto treatment equipment with which many patients requiring similar treatments can be looked after. Examples are in dialysis clinics, in which many patients can be treated with different types of blood purification, for example by haemodialysis, haemodiafiltration, peritoneal dialysis, haemoultrafiltration, etc.

With such treatments, it must ensured that a patient receives only the appropriate treatment.

Until now, the treatment data has had to be entered. However, this is time-consuming and is open to parameters being entered incorrectly. In other words, an incorrect entry could result in parameters being set that are unsuitable for the patient. The consequence could be shock or serious injury.

OBJECT OF THE INVENTION

Thus, it is an object of the invention to provide a system and a method by means of which a medical treatment can be provided with enhanced safety for the patient.

BRIEF DESCRIPTION OF THE INVENTION

The object of the invention is achieved by means of a medical treatment system. The medical treatment system comprises a medical treatment device and a therapy-enabling device.

The medical treatment device comprises input means for selecting a treatment, wherein the medical treatment device furthermore comprises a device for generating a patient-related and a treatment-related request code, wherein the request code is presented on the medical treatment device.

The therapy-enabling device comprises a device for receiving request code data, wherein the therapy-enabling device furthermore comprises an enabling code generating device which, as a function of a received request code and stored data, decides whether an enabling code will be generated and sends the generated request code.

Furthermore, the medical treatment device comprises means for inputting an enabling code wherein, as a function of the enabling code and optionally the previously generated request code, a decision is made as to whether the requested treatment will be enabled.

The object of the invention is also achieved by means of a corresponding method carried out on the medical treatment device or on the therapy-enabling device.

Further advantageous embodiments form the subject matter of the dependent claims and the detailed description.

BRIEF DESCRIPTION OF THE DRAWINGS

The invention will now be described in more detail with reference to the accompanying drawings, in which.

DETAILED DESCRIPTION

The invention will now be described in more detail with reference to the figures. It should be noted in this regard that various aspects will be described which may be employed individually or in combination. This means that any of the aspects may be employed in different embodiments, unless explicitly described as being a pure alternative.

Furthermore, for the sake of simplicity, as a rule, reference will only be made to one entity. Unless explicitly stated otherwise, however, the invention may also comprise a plurality of the entities in question. In this regard, the use of the words "a" or "an" should be understood to mean that in a single embodiment, at least one entity is used.

Figure 1:
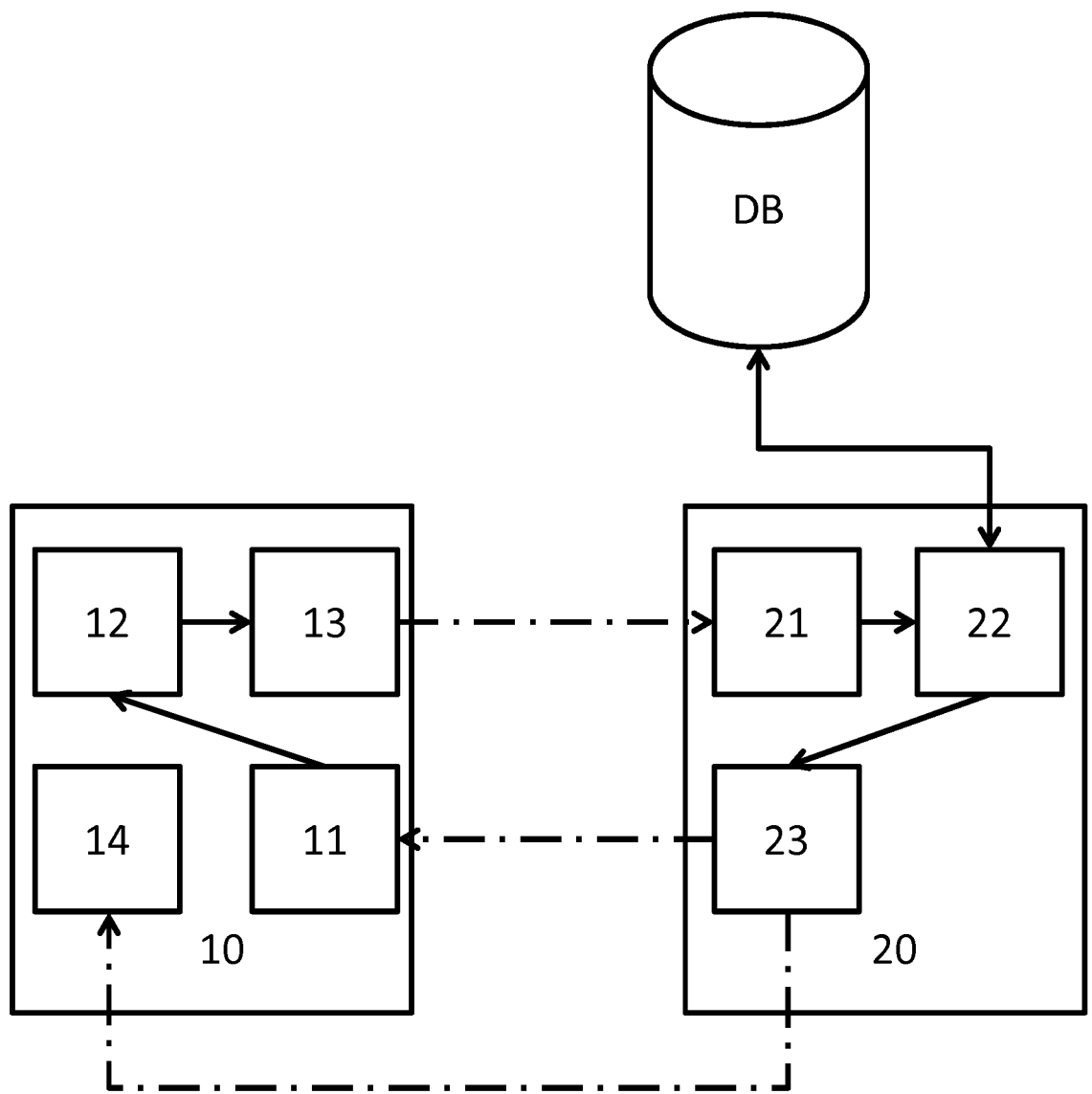
FIG. 1 is a diagrammatic overview of systems in accordance with embodiments of the invention.

FIG. 1 is a diagram of a medical treatment system. The medical treatment system 1 comprises a medical treatment device 10 and a therapy-enabling device 20. Although both the medical treatment device 10 and the therapy-enabling device 20 will be described hereinafter as a unit, this is not an essential feature, and so each device may also be configured in a modular manner or separated in space.

The medical treatment device comprises input means 11 for selecting a treatment. In this regard, the input means may, for example, be a typical means for inputting by means of a switch, push-button, rotary selector, graphical user interface of a touchscreen, keyboard, trackball, mouse, etc., but may also be an input using a smartcard reader, etc. In other words, all that is required is that data pertaining to a patient and the treatment requested for the patient can be made available to the medical treatment device 10. It should be noted in this regard that it is also possible, for example, for patient data to be entered with a first input means and for the requested treatment data to be entered with a second input means 11. Entering may be carried out by the patient and/or by medically qualified specialist or support staff.

The medical treatment device 10 also comprises a device 12 for generating a patient-related and a treatment-related request code. As an example, the device 12 for generating a patient- and treatment-related request code may be a computer or a microprocessor, a microcontroller, an appropriately configured ASIC (application-specific integrated circuit) or a FPGA (field programmable gate array).

The request code which is generated in this manner is presented to the medical treatment device 10 at 13. This may be provided in any manner and will be discussed further hereinbelow.

The request code which is generated is then transmitted to the therapy-enabling device 20.

As an example, the patient or the medically qualified specialist or support staff can read off/enter a code using a smart phone and (for example by means of a special application) send it to the therapy-enabling device 20.

In turn, the therapy-enabling device 20 comprises a device 21 for receiving the request code data. The receiving device 21 can receive if it comprises, for example, a data interface such as a network and/or modem interface, or indeed input means—as already discussed above in connection with the medical treatment device 10.

The medical treatment device 10 and the therapy-enabling device 20 are in this case disposed in a manner that is separated in space from each other. As an example, a therapy-enabling device 20 may provide services—as will be described below—for a plurality of medical treatment devices 10.

Furthermore, the therapy-enabling device 20 comprises an enabling code generating device 22 which, as a function of a received request code and of stored data, wherein patient- and/or treatment-related data are stored in a local or remote database DB and which can be called up therefrom, decides whether an enabling code will be generated, and then sends the generated request code by means of an appropriate transmitting device 23. As an example, the enabling code generating device 22 may be a computer or a microprocessor, a microcontroller, an appropriately configured ASIC (application-specific integrated circuit) or a FPGA (field programmable gate array).

The transmission device 23 may, for example, be provided with a data interface such as, for example, a network and/or modem interface. As an example, the transmission device 23 and the receiving device 21 may be parts of a common data interface.

The data may be sent directly to the medical treatment device 10, or indeed to a device in the vicinity thereof.

As an example, the enabling code may inform the patient or the medically qualified specialist or support staff that it has sent the request code or indeed has stored it in the database. Furthermore, the medical treatment device 10 is also provided with means for inputting an enabling code 11 or 14 wherein, as a function of the enabling code and optionally the request code which has been generated by the medical treatment device 10, a decision is made as to whether the requested treatment will be enabled.

In other words, by means of the request code in which the patient and the requested treatment are encoded, the therapy-enabling device is placed in the position whereby the requested treatment can be compared with the patient data and the stored data. In this manner, for example, it can be confirmed that the requested treatment data matches with the data stored for a patient, for example that a specific treatment plan is being complied with or indeed that the requested treatment falls within a specified range for the stored data.

In other words, it can be ensured that a patient receives only the appropriate treatment.

In this manner, incorrect entries can be avoided, whereupon patient safety is enhanced.

In addition, the system also allows the requested treatments to be logged so that, for example, a course of therapy can be assessed. This generates the possibility of quality control.

Other parameters which are patient- and/or treatment-related may also be taken into account when making the enabling decision.

In one embodiment of the invention, the request code comprises data selected from a group comprising: patient identity data, patient condition data, treatment parameters, device parameters, and parameters concerning consumables.

Examples of patient identity data are identification numbers such as social security or health insurance number, name, first name, date of birth, etc., which allow the patient to be uniquely identified. Appropriate data are also stored in the local or remote database DB, in order to allow correlation of the data sets.

Examples of patient condition data include weight, height, heart rate, blood pressure, blood sugar, haemoglobin, haematocrit, relative blood volume, lung volume, etc. In other words, all patient condition data of relevance to a treatment can also be transmitted.

Examples of treatment parameters are the requested type of a treatment such as, for example, haemodiafiltration, haemodialysis, ultrafiltration, etc. As an example, some medical treatment devices 10 authorize a plurality of treatments, and so it is important to communicate the requested treatment (for example haemodialysis) as well as, if appropriate, the respective parameters for the selected treatment such as, for example, the duration of the treatment, the set blood pump rate, the set dialysate pump rate, the substitution volume and rate, the ultrafiltration volume and rate, etc.

Examples of device parameters are the condition and/or device property data (type of machine, identification number, equipment) which allows the therapy-enabling device 20 to decide whether a requested treatment can in fact (still) be carried out by the device.

Examples of consumable parameters are data relating to dialysis fluids (type and composition of the dialysis fluid and/or substitution fluid), the dialysis machine, the disposable articles used such as tube sets, dialysis filters, etc.

In general, the data include at least as many characteristic features as are necessary to be able to unequivocally assign a treatment to a patient.

In one embodiment of the invention, the request code is graphically coded on the medical treatment device 10, for example on a screen.

In this regard, the request code may, for example, be selected from a group comprising QR codes, barcodes, and flicker codes. In this manner, one or multi-dimensional codes may be employed.

In other words, the request code may, for example, be provided on a screen 13 on the medical treatment device 10. As an example, the patient or the medically qualified specialist or support staff can read off/enter the request code using a smart phone (for example by using a special application) and transmit to the therapy-enabling device 20. In this manner, the mobile phone number or MAC address of the smart phone may also serve as an (additional) identification of the patient or the medically qualified specialist or support staff. This greatly simplifies the operation.

In one embodiment of the invention, the request code comprises an encryption, for example as a secure QR code. In this manner, on the one hand, data safety having regard to personal data of the patient is improved, and on the other hand, the overall security of the data communication is improved.

In a further embodiment, the input means 11 or 14 is selected from a group comprising a card reader, graphical user interface and near field communication reader. In other words, data can be entered using multiple technologies so that, for example, an interaction with the health card (card reader) which has been introduced in Germany is possible via a card reader 14, as well as with an electronic passport (NFC, RFID) or a smart phone (NFC, Bluetooth, ZigBee, WLAN). As well as inputting from a touch screen 11. In other words, information can also be exchanged as an alternative to or in addition to graphical coding via near field communication (NFC, RFID) from the medical treatment device 10 to, for example, a mobile device and vice versa. This renders scanning and manually entering the activation code redundant.

In a further embodiment, in the case in which a requested treatment is declined, a request for issuing a qualified request code by medically qualified staff is sent as the enabling code.

In other words when, for example, a treatment falls outside the given parameters, but appears reasonable from a local examination, that enabling should be activated. On the other hand, if the response shows up a possible incorrect entry for the on-site patient and/or the medical specialist or support staff, or authorizes an examination of the state of health, then for example, patient condition data could contraindicate carrying out the requested treatment. The treatment will only be enabled by entering a qualified request code.

In an advantageous embodiment, the qualified request code may also, for example, comprise the identification as medically qualified staff.

In particular, the qualified request code may also comprise the identification of the medically qualified staff, selected from the group formed by a finger scan, iris scan, or PIN. In this regard, for example, an optical reading device may be provided as the input means 11. Naturally, a patient may also be identified in a similar manner. It should be noted in this regard that, for example, it may be provided that the level of qualification increases with the degree of a discrepancy from predetermined values/ranges of values so that, for example, small discrepancies can be enabled by local medical auxiliary staff using a qualified request code (local or with the aid of the therapy-enabling device 20), while larger discrepancies can only be enabled by a qualified request code given by local medically qualified specialist staff (locally or with the aid of the therapy-enabling device 20).

In one embodiment of the invention, (qualified) request codes and/or enabling codes are exchanged by means of a wireless or wired communication network. Examples of communication networks are LANs (local area networks), WANs (wide area networks) and also WLANs (wireless LANs), as well as mobile phone networks such as LTE, UMTS/GSM networks, for example.

In a further embodiment of the invention, for example, in emergencies or when an intervention on the therapy-enabling device 20 is not possible, a requested treatment could be enabled locally, wherein in the case of local enabling, for example, entering an emergency TAN is necessary. In other words, for example in an emergency and/or when the therapy-enabling device 20 cannot be accessed, then the local medically qualified staff can still enable an (urgently) required treatment as an exception. In this regard, for example, only a limited emergency operation might be provided rather than the full range of treatments available. Furthermore, specific treatments might only be enabled by medically qualified staff.

In a further embodiment of the invention, moreover, the enabling code generating device 22 may decide, as a function of a received request code and stored data, whether a requested treatment is plausible for the patient and an enabling code could only be generated when the requested treatment is plausible for the patient. The test of plausibility could comprise comparing the requested treatment with previous treatments of a specific patient. If the treatments or their parameters differ substantially from each other and/or if the treatment contravenes medical guidelines, then the requested treatment is not plausible, and the consequence could be that an enabling code will not be generated. Checking the (medical) plausibility may be carried out by an expert system which is present in the therapy-enabling device 20 or in another device which can interact with the therapy-enabling device 20.

Without loss of generality, the invention can be used on a multitude of different treatment systems. However, in particular, the medical treatment device 10 is a blood treatment device selected from the group which in particular comprises a dialysis device, a plasmapheresis device, an apheresis device, haemodiafiltration, haemoultrafiltration, haemoperfusion, peritoneal dialysis and albumin dialysis.

Figure 2:
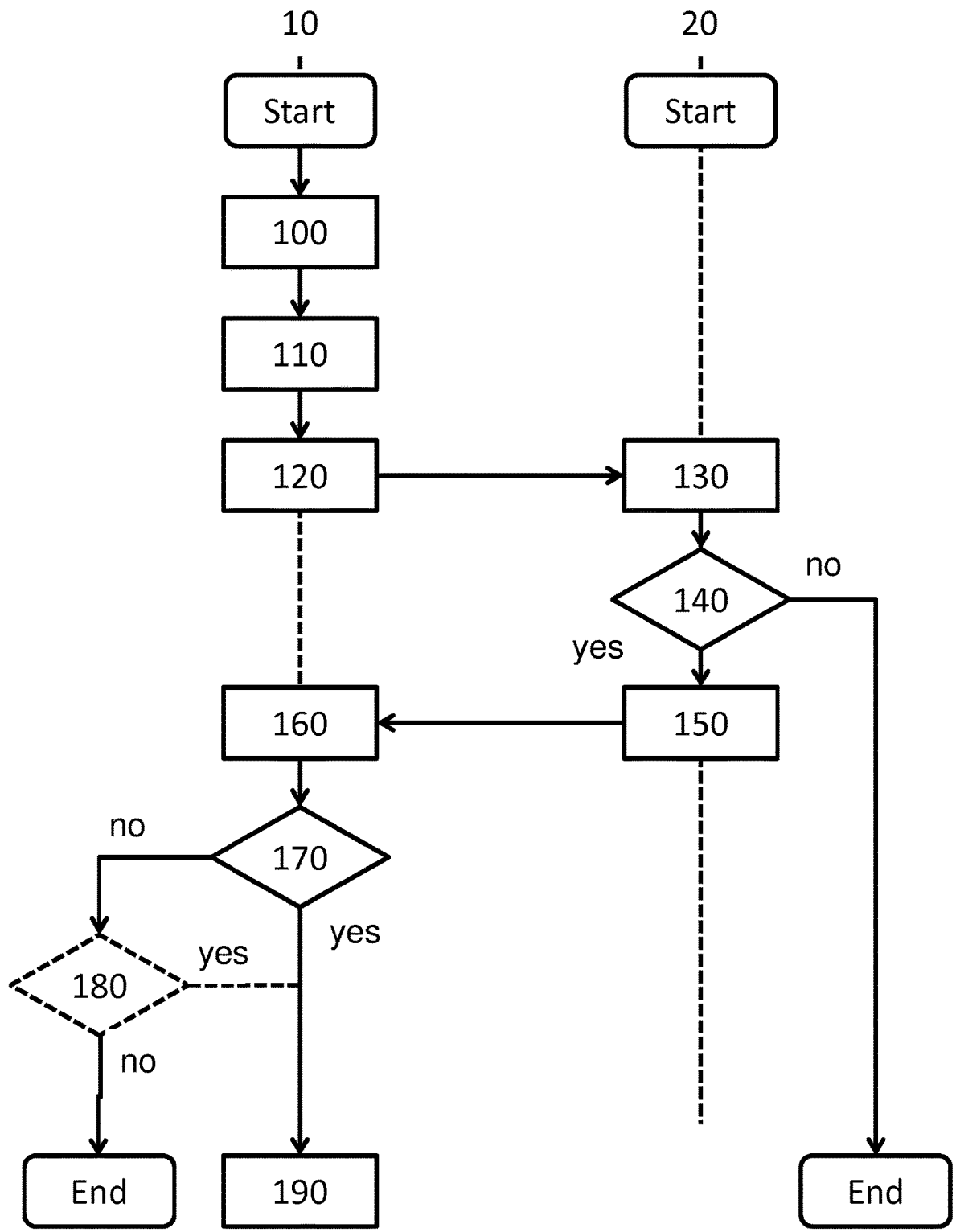
FIG. 2 shows a diagrammatic flow chart for methods in accordance with embodiments of the invention.

Clearly, the above description also provides a possible embodiment of the method as shown in FIG. 2.

In a first step 100, a treatment and, if appropriate, treatment parameters are selected on the medical treatment device. Together with patient data, which can equally be entered or read in, in a step a patient- and treatment-related request code is generated by the medical treatment device 10 and the request code is generated in step 120.

The prepared request code is transmitted to the therapy-enabling device 20 and received thereby in step 130. Next, in step 140, as a function of the request code which is received and stored data—retrieved from the database DB—a decision is made as to whether an enabling code will be generated. In the case in which an enabling code is generated, in step 150 the enabling code which is generated is sent via the therapy-enabling device 20 in the direction of the medical treatment device 10. Optionally, the enabling code may also contain the request for qualified enabling. If not enabled, the program can be terminated. Alternatively or additionally, a "enabling code" may be generated which indicates that the request is declined and provides the reason for declining. In other words, the appropriate error message can be displayed on the medical treatment device 10.

The transmitted enabling code can then in general be received by the medical treatment device 10 in step 160. Henceforth, in step 170, as a function of the enabling code and the previously generated request code, a decision can be made by the medical treatment device 10 as to whether the requested treatment is to be enabled.

If the request treatment is enabled, then in step 190, the treatment can be started. Following a completed treatment, this fact could be transmitted to the therapy-enabling device 20 for optional logging together with further run data for the completed treatment.

If the requested treatment is not enabled then, for example, emergency enabling and/or qualified enabling may be provided in an optional step 180. In this regard, for example, a certain number of treatments may be possible by entering a TAN, for example from a list, and/or a TAN may be received by an emergency hotline.

If (qualified) enabling is not granted, then the program can be terminated.

It may be the case that between preparation of a request code in step 120 and receipt of an enabling code in step 160, a maximum time period cannot be exceeded in order, for example, not to block a medical treatment device 10 if there is no response, for example as a consequence of communication problems or failure of the therapy-enabling device 20. This means that after a predetermined time period has expired, the medical treatment device 10 automatically assumes that the enabling code is incorrect and will expect an input in step 180.

Here again, a time limit may be provided so that the method has a finite end.

The invention may also be incorporated into one or more computer program products in order to program devices of a medical treatment system for carrying out steps of a method. In this regard, computer program products may be provided as downloadable streams of data or indeed as a data carrier, for example DVD, CD, memory card, or memory chip.

We shall now describe the invention once again in the case of an application.

If a patient is about to be treated, the treatment data are entered into the medical treatment device 10, for example a dialysis device. A GUI (graphical user interface) may be used for entry. Patient data and/or also treatment data may, however, also be communicated to the medical treatment device via mobile data storage, such as patient cards (smart cards) and appropriate readers.

Software provided in the medical treatment device 10 transforms these data into an (encrypted) graphical code. This code may, for example, be entered via a smart phone and be encrypted and decoded by software (an app). The data are then transmitted to the therapy-enabling device 20 (via a mobile phone network, internet, etc.), where they are checked as a treatment request.

If the data check shows that the requested treatment complies with specific criteria, an enabling code is sent back to the mobile device (for example TAN). This enabling code allows the medical treatment device 10 to be unlocked so that the treatment can then be carried out.

Many criteria can be checked in the therapy-enabling device 20.

Furthermore, however, an expert system may also be stored in the therapy-enabling device 20, which checks more criteria, for example whether the requested treatment is medically consistent or, on the other hand, the treatment poses potential risks. A medically inconsistent procedure may, for example, be a treatment where the patient condition data contraindicates a treatment on the grounds of clinical considerations.

In one embodiment, for such a failure of the criterion check, in step 150, instead of sending back an enabling code, an error or alarm message could be sent.

In one embodiment, the criterion check may also, however, lead to the enabling code generating device deciding, as a function of a received request code and stored data, whether a requested treatment is plausible for the patient and, if the requested treatment is not plausible for the patient, the enabling code can be supplemented by data so that a plausible treatment can be enabled. These data may include absolute data as well as relative difference data so that, for example, only the discrepancy in the data with respect to the requested treatment is transmitted. In this regard, for example, an incorrect entry is recognized (and possibly also signalled by an error or alarm message), and then a treatment which appears to be medically sensible can be proposed. The proposed treatment can then be displayed on the medical treatment device 10 (for example together with the error or alarm message). Next, the modified treatment can be enabled by the appropriate staff. In other words, the medical treatment device 10 decides, at least as a function of the enabling code, whether and how the requested treatment will be enabled.

In a further embodiment, in such a case, however, a valid activation code can be requested by qualified medical staff, wherein the qualified medical staff member identifies him/herself, for example by entering a personal identification number on the mobile device (for example by means of a finger scanner, iris scanner or other biometric data which uniquely identifies a person), and then after successfully checking the qualification of the requesting person, a valid activation code can be generated despite the concerns communicated by the expert system.

In this regard, "overruling" the concerns of the expert system depends on the qualification of the operator. As an example, doctors have a higher overruling capability than nurses.

Advantageously, a procedure of this type is logged, i.e. the person overruling the expert system or trying to overrule the expert system can be identified at all times.

Advantageously, all procedures are logged in connection with enabling the treatment.

In one embodiment, the activation code which is expected from the medical treatment device 10 to enable the treatment may be computed from the entered data by software. One advantage of this embodiment is thon the medical treatment device 10 itself does not require an external data link, which increases data security. In other words, when an interface does not have direct communication, then the safety of the medical treatment device 10 is enhanced.

The activation code can in this case be computed, as an example, by specific algorithms (for example a key generator) which generates unique activation codes (for example, optically coded codes such as QR codes, flicker codes) from the input data.

In a further embodiment in which the medical treatment device comprises a data link option (internet, mobile phone network etc.), the activation code may be randomly generated by the therapy-enabling device 20 and communicated to the medical treatment device 10 by data transfer.

Here again, with a medical treatment device 10 equipped in this manner, the described request for a activation code may advantageously be made via a mobile device.

In this case, the mobile device functions almost as a key for the medical device, wherein the key can be uniquely assigned (for example by transmitting device identification numbers and entering personalized PINs or by entering biometric data). Only qualified persons receive the key, in which the software with the functionality described above has to be registered in a personalized manner.

The invention claimed is:

1. A medical treatment system, comprising
   a medical treatment device, wherein the medical treatment device comprises input means for selecting a requested treatment, a display screen, a lock for locking-out the medical treatment device from carrying out treatments, and a computer for generating a patient-related and a treatment-related request code pertaining to the requested treatment and transmitting the request code to a therapy-enabling device, wherein the request code is presented on the display screen of the medical treatment device,
   a therapy-enabling device, wherein the therapy-enabling device comprises a data interface for receiving a request code from the medical treatment device, wherein the therapy-enabling device furthermore comprises an enabling code generating device selected from the group consisting of a computer, a microprocessor, a microcontroller, an appropriately configured application-specific integrated circuit (ASIC), and a field programmable gate array (FPGA), wherein, as a function of a received request code and as a function of stored data, the enabling code generating device decides whether an enabling code will be generated, and, if it is decided that an enabling code will be generated, generates and sends an enabling code,
   wherein the input means of the medical treatment device is further configured for entering an enabling code,
   wherein the medical treatment device decides, at least as a function of the enabling code, whether, and if necessary how, the requested treatment will be enabled, and
   wherein, the medical treatment device is configured such that, if the medical treatment device decides that the requested treatment will be enabled, the medical treatment device unlocks the lock.

2. The medical treatment system as claimed in claim 1, wherein the request code comprises data selected from a group comprising: patient identity data, patient condition data, treatment parameters, device parameters, and parameters concerning consumables.

3. The medical treatment system as claimed in claim 1, wherein the request code is coded graphically.

4. The medical treatment system as claimed in claim 1, wherein the request code is selected from a group consisting of QR codes, bar codes, and flicker codes.

5. The medical treatment system as claimed in claim 1, wherein the request code comprises an encryption.

6. The medical treatment system as claimed in claim 1, wherein the input means is selected from a group consisting of a card reader, a graphical user interface, and a near field communication reader.

7. The medical treatment system as claimed in claim 1, wherein, in the case in which a requested treatment is declined, the enabling code comprises a request for issuing a qualified request code by medically qualified staff.

8. The medical treatment system as claimed in claim 7, wherein the qualified request code also comprises an identification as to a qualification of who qualifies as medically qualified staff.

9. The medical treatment system as claimed in claim 7, wherein the qualified request code also comprises an identification of the medically qualified staff, which is selected from the group consisting of a finger scan, an iris scan, or a PIN.

10. The medical treatment system as claimed in claim 1, wherein each of a request code and an enabling code is exchanged by means of a wireless or wired communication network.

11. The medical treatment system as claimed in claim 1, wherein the medical treatment system is configured to locally enable a requested treatment on the medical treatment device, and an emergency TAN is required for local enabling.

12. The medical treatment system as claimed in claim 1, wherein the medical treatment system is configured to locally enable a requested treatment on the medical treatment device.

13. The medical treatment system as claimed in claim 1, wherein the enabling code generating device decides, as a function of a received request code and stored data pertaining to a patient, whether a requested treatment is plausible for the patient, and an enabling code is only then generated when the requested treatment is plausible for the patient.

14. The medical treatment system as claimed in claim 13, wherein a decision as to whether a requested treatment is plausible includes:
  comparing the requested treatment with previous treatments and/or parameters thereof, wherein, if the treatments or parameters thereof differ substantially from each other, the requested treatment is not plausible, and/or
  checking the medical plausibility by means of an expert system wherein, when the treatment contravenes medical guidelines, the requested treatment is not plausible.

15. The medical treatment system as claimed in claim 1, wherein the enabling code generating device decides, as a function of a received request code and stored data pertaining to a patient, whether a requested treatment is plausible for the patient, and, if the requested treatment is not plausible for the patient, the enabling code is supplemented by data so that a plausible treatment can be enabled.

16. A blood treatment device for a medical treatment system as claimed in claim 1, wherein the blood treatment device is a device selected from the group consisting of a dialysis device, a plasmapheresis device, an apheresis device, a haemodiafiltration device, a haemoultrafiltration device, a haemoperfusion device, a peritoneal dialysis device, and an albumin dialysis device.

17. The medical treatment system as claimed in claim 1, wherein the enabling code generating device is a computer.

18. A method for use with a medical treatment system comprising a medical treatment device and a therapy-enabling device, the method comprising the following steps:
  selecting a requested treatment on the medical treatment device,
  generating a patient- and treatment-related request code and transmitting the request code, via the medical treatment device, to the therapy-enabling device,
  receiving the request code on the therapy-enabling device,
  deciding, via the therapy-enabling device, as a function of a received request code and stored data, to generate an enabling code,
  generating an enabling code,
  sending the enabling code which is generated, via the therapy-enabling device, to the medical treatment device,
  receiving the generated enabling code on the medical treatment device,
  deciding, via the medical treatment device as a function of at least the enabling code and the previously generated request code, that the requested treatment will be enabled, and
  unlocking a lock that otherwise prevents the medical treatment device from carrying out the requested treatment.

19. A method for use with a medical treatment device in a medical treatment system, the medical treatment system comprising the medical treatment device and a therapy-enabling device, the method comprising the following steps:
  receiving a selection of treatments on the medical treatment device,
  selecting a requested treatment from the selection of treatments,
  generating a patient- and treatment-related request code and presenting the generated request code via the medical treatment device,
  receiving a generated enabling code on the medical treatment device,
  deciding, via the medical treatment device, as a function of the generated enabling code and the generated request code, that the requested treatment will be enabled, and
  unlocking a lock that otherwise prevents the medical treatment device from carrying out the requested treatment.

20. A method for a medical treatment device in a medical treatment system comprising a medical treatment device and the therapy-enabling device, comprising the following steps:
  receiving a request code at the therapy-enabling device,
  deciding, as a function of a received request code and stored data, that an enabling code will be generated,
  generating the enabling code,
  sending the generated enabling code via the therapy-enabling device to the medical treatment device, and
  based on the generated enabling code, unlocking a lock that otherwise prevents the medical treatment device from carrying out the requested treatment.

* * * * *